US 6,673,092 B1

(12) United States Patent  (10) Patent No.: US 6,673,092 B1
Bacher                     (45) Date of Patent:     Jan. 6, 2004

(54) MEDICAL FORCEPS WITH TWO INDEPENDENTLY MOVEABLE JAW PARTS

(75) Inventor: Uwe Bacher, Tuttlingen (DE)

(73) Assignee: Karl Storz GmbH & Co. KG (DE)

(*) Notice: Subject to any disclaimer, the term of this patent is extended or adjusted under 35 U.S.C. 154(b) by 662 days.

(21) Appl. No.: 09/644,996

(22) Filed: Aug. 24, 2000

Related U.S. Application Data

(63) Continuation of application No. PCT/EP99/04685, filed on Jul. 6, 1999.

(30) Foreign Application Priority Data

Jul. 25, 1998 (DE) ......................................... 198 33 600

(51) Int. Cl.$^7$ ............................................. A61B 17/42
(52) U.S. Cl. ......................... 606/205; 606/206; 606/207
(58) Field of Search ................................. 606/205–208; 600/104; 81/345–351

(56) References Cited

U.S. PATENT DOCUMENTS

| 5,100,421 A |   | 3/1992  | Christoudias ............... 606/147 |
| 5,147,373 A |   | 9/1992  | Ferzli ......................... 606/144 |
| 5,171,257 A |   | 12/1992 | Ferzli ......................... 606/205 |
| 5,192,298 A | * | 3/1993  | Smith et al. ................. 606/205 |
| 5,368,606 A |   | 11/1994 | Marlow et al. ............. 606/170 |
| 5,403,332 A |   | 4/1995  | Christoudias ............... 606/148 |
| 5,527,339 A |   | 6/1996  | Koscher et al. ............. 606/205 |
| 5,630,832 A |   | 5/1997  | Giordano et al. ........... 606/208 |

FOREIGN PATENT DOCUMENTS

| EP | 0640319 A1  | 7/1994 |
| WO | WO95/29641  | 4/1995 |

* cited by examiner

Primary Examiner—Julian W. Woo
Assistant Examiner—P Roberts
(74) Attorney, Agent, or Firm—St. Onge Steward Johnston & Reens LLC

(57) ABSTRACT

A medical forceps is provided with two independently moveable jaw parts at the distal end. The forceps comprise a shaft with two rods extending axially therein, the rods being arranged adjacent to one another and being axially displaceable independently of one another. The first rod is joined to the first jaw part and the second rod to the second jaw part. The forceps further comprise a handle at the proximal end with two actuator elements, wherein the first actuator element is joined to the first rod and the second actuator element to the second rod. The first rod and the second rod each comprise a coupling element at their proximal ends. The first actuator element and the second actuator element each comprise a substantially complementary coupling element at their distal ends, such that the coupling elements of the rods are engageable in force-locking, but releasable manner with the coupling elements of the actuator elements by axially pushing the rods and the actuator elements together and/or by commonly rotating the two rods about a longitudinal axis of the shaft.

26 Claims, 5 Drawing Sheets

MEDICAL FORCEPS WITH TWO INDEPENDENTLY MOVEABLE JAW PARTS

CROSS REFERENCE TO PENDING APPLICATION

This application is a continuation of pending International Application PCT/EP99/04685, filed Jul. 6, 1999 designating the United States.

BACKGROUND OF THE INVENTION

The invention generally relates to a medical forceps comprising two independently moveable jaw parts at a distal end of a shaft in which two rods extend axially, which are arranged adjacent to one another and are axially displaceable independent of one another. The first rod is joined to the first jaw part and the second rod is joined to the second jaw part. A handle is provided on the proximal end having two actuator elements, where the first actuator element is joined to the first rod and the second actuator element is joined to the second rod.

Forceps of this type are disclosed in U.S. Pat. No. 5,403,332 or in U.S. Pat. No. 5,171,257. Forceps of the above-mentioned type are normally used in endoscopic surgery as multifunctional instruments, for example to cut tissue with the first jaw part and to grasp the tissue from the other jaw part for removal of the tissue from the body. Accordingly, the first jaw part is formed as a cutting tool, while the other jaw part is configured as a grasping tool. Both jaw parts are moveable independent of one another, i.e. they can be independently opened and closed. For this purpose, the forceps comprise an actuator element for each jaw part, with which the corresponding jaw part can be opened or closed.

Two rods arranged axially adjacent to one another are provided in the shaft for transmitting force from the actuator elements to the jaw parts. The first rod at its proximal end is coupled to the first actuator element and at its distal end to the first jaw part and the second rod is coupled at its proximal end to the second actuator element and at its distal end to the second jaw part in force-locking manner. The two rods operate to close and open the jaw parts in response to tension or pressure.

A disadvantage of the known forceps is that neither the rods nor the shaft can be removed from the handle, whereby the forceps are not accessible to thorough cleaning or only accessible with difficulty. However, when using such forceps in a surgical operation, impurities collect between the shaft and the rods. A flushing opening is provided between the handle and the shaft in the known forceps, through which flushing fluid can be introduced into the shaft for cleaning the shaft interior. However, a thorough cleaning of the shaft interior and the rods extending therein is not guaranteed by introducing a cleaning fluid, because for example pieces of tissue having entered the shaft can remain adhered to the adjacent rods or on edges or in recesses, which cannot be removed by the cleaning fluid.

The object of the invention is therefore to provide an improved medical forceps of the mentioned type, in which the forceps can be disassembled for cleaning, where the rods are removable from the handle and where- the forceps after cleaning should be rapidly available for repeated use and should be easy to reassemble.

SUMMARY OF THE INVENTION

According to the present invention, a medical forceps is provided, comprising:
  a shaft having a distal end and a proximal end;
  a first and a second jaw part disposed at said distal end of said shaft and being movable independently from each other;
  a handle disposed at said proximal end of said shaft having a first and a second actuator element;
  a first and a second rod extending through said shaft and being arranged adjacent to one another and being axially displaceable independently from one another, said first rod being joined to said first jaw part and to said first actuator element and said second rod being joined to said second jaw part and to said second actuator element,
  wherein said first rod and said second rod each comprise a coupling element at a proximal end of said first and second rod, said first actuator element and said second actuator element each comprise a coupling element at a distal end of said first and second actuator element, said coupling elements of said actuator element being substantially complementary to said coupling elements of said rods such that said coupling elements of said rods are engageable in force-locking, but releasable manner with said coupling elements of said actuator elements by axially pushing said rods and said actuator elements together and/or by commonly rotating said rods about a longitudinal axis of said shaft.

The medical forceps according to the present invention thus provide that the rods are configured to be removable from the handle, for which purpose the proximal ends of the rods and the distal ends of the actuator elements comprise coupling elements which are substantially complementary to one another and are releasable from one another. The coupling mechanism of the forceps according to the invention has a constructively simple configuration and allows a simple manual operation, because the connection of the rods with the actuator elements is accomplished with simple manipulations, namely by pushing the rods together and/or by rotating the rods.

This coupling mechanism is also advantageous because no securement means are needed to couple the rods with the actuator elements, for example screws, so that no tools such as a screwdriver is necessary to assemble the forceps for renewed use. Axially pushing and/or rotating are very simple manipulations.

The present medical forceps can be thoroughly cleaned after removing the rods, because the removed and therefore accessible rods can be separately washed, so that impurities or contamination collected in intermediate spaces between the rods or at the edges can be reliably removed.

The coupling elements can be complementary round structures, for example spherical or ball-joint structures. The structures may also not be round, for example wedge-shaped structures having counterengaging sections so that tension and compression forces from the actuator elements are transmitted to the rods. The rods themselves can have any suitable cross sectional shape, for example round or not round, for example rectangular.

In a preferred embodiment of the forceps according to the present invention, the coupling elements of the rods and the coupling elements of the actuator elements are configured such that they are disengageable by a rotation of the rods about the mentioned longitudinal axis.

This has the further advantage that the rods can be released in simple manner without the necessity of using tools or the like. The further advantage of the coupling mechanism, releasable by rotating the rods, is the particularly simple constructive design of the present forceps.

In a further preferred embodiment, the coupling elements of the rods become lockingly engaged with the coupling elements of the actuator elements by actuating the actuator elements and/or by actuating the jaw parts.

An advantage here is that the force-locking connection of the rods and the actuator elements is accomplished by actuating the actuator elements through grips normally provided on the handle, which are connected with the actuator elements, whereby the connection of the actuator elements with the rods is accomplished in particularly simple and reliable manner. The actuator elements can be displaced relative to the rods by actuating the actuator elements, where the rods connected to the jaw parts can be displaced relative to the actuator elements by actuating the jaw parts.

In a further preferred embodiment, the coupling elements of the rods and/or the coupling elements of the actuator elements comprise engagement slopes.

This has the advantage that the coupling elements of the rods and the coupling elements of the actuator elements are forcibly guided when axially pushed together, by which the coupling elements of the rods self-engage with the coupling elements of the actuator elements when pushed together, without having to first actuate a catch or the like.

It is preferred in this context that the rods are slightly elastically bendable at their proximal end.

This has the advantage that the rods in this configuration are sufficiently bendable on the one hand so that the coupling elements can glide along the engagement slopes without increased frictional resistance, where the proximal ends of the rods are deflected from their longitudinal axis. On the other hand, the coupling elements of the rods after overcoming the engagement slopes then engage elastically and lockingly with the coupling elements of the actuator elements and establish a force-locking connection between the rods and the actuator elements.

In a further preferred embodiment, the rods are restricted against undesired rotation when the coupling elements of the rods are engaged with the coupling elements of the actuator elements.

This feature is of advantage, especially with the above-mentioned embodiment where the coupling elements of the rods are disengageable from the coupling elements of the actuator elements by rotating the rods about the longitudinal axis, because this prevents the rods from being released from the actuator elements during use of the forceps in a surgical operation, whereby the operational safety of the forceps is improved.

In a further preferred embodiment, the shaft is releasably joined to the handle.

This feature provides the further advantage that not only the rods are removable from the handle and therefore can be cleaned separately, but also the shaft can be removed so that it can also be thoroughly cleaned, particularly its interior.

Preferably the shaft is joined to the handle by means of a locking mechanism arranged on the handle.

This has the advantage that the shaft is also connectable and removable from the handle in a simple manner, where the locking mechanism guarantees a reliable interconnection between the handle and the shaft during use of the forceps.

In a further preferred embodiment, the locking mechanism secures the shaft against rotation.

This feature has the further advantage that the shaft is secured against rotation without further constructive means as soon as the shaft is locked on the handle, whereby further parts for securing against rotation are saved.

In a further preferred embodiment, the shaft is removable from the rods and the rods are secured against rotation with the shaft in the assembled condition.

This feature has the advantage that the forceps according to the invention can be further disassembled, so that the cleaning capabilities of the present forceps are further improved. The further advantage of this feature is that the rods are already secured against rotation by the shaft, with which they are joined in assembled condition, so that further means for securement against rotation of the rods is not necessary, which reduces the complication of the structure of the present forceps.

In a further preferred embodiment, the coupling elements of the rods are formed as heads and the coupling elements of the actuator elements are formed as bore holes substantially complementary thereto, which are open at a distal front face of the actuator elements and open to the side, or vice versa.

This feature allows a constructively very simple configuration of the coupling elements of the rods as well as the coupling elements of the actuator elements, which in the connected condition also guarantees a mechanically reliable closed linkage between the rods and the actuator elements. The heads are preferably provided as balls and the bore holes formed as ball sockets. Clearly it is also possible to provide the heads on the actuator elements and the bore holes on the rods.

Preferably, the side opening of the first ball socket-faces in the opposite direction with respect to the side opening of the second ball socket.

This feature is of advantage, in particular in conjunction with the mentioned coupling mechanism, where the coupling elements of the rods are engaged and disengaged with the coupling elements of the actuator elements by rotating the rods about the longitudinal axis. This configuration however also makes it possible to engage the coupling elements of the rods with the coupling elements of the actuator elements by axially pushing the elements together.

Further advantages will become apparent from the following description and the appendant drawing. It will be understood that the above-mentioned features and those to be discussed below are not only applicable in the given combinations, but may also be employed in other combinations or taken alone without departing from the scope of the present invention.

An embodiment of the invention is illustrated in the drawings and will be discussed in the following with reference to the figures.

BRIEF DESCRIPTION OF THE DRAWINGS

Figure 1:
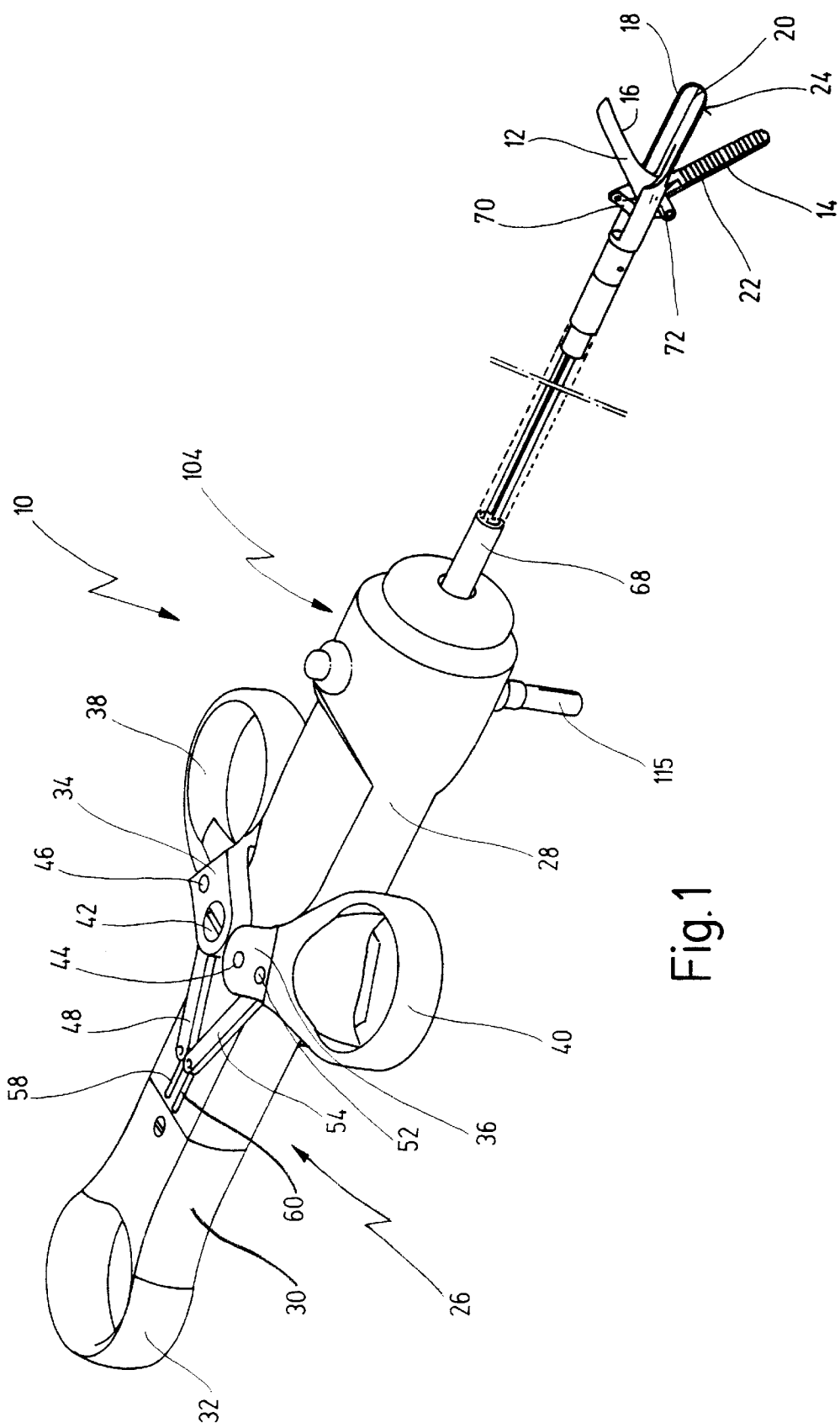
Figure 2:
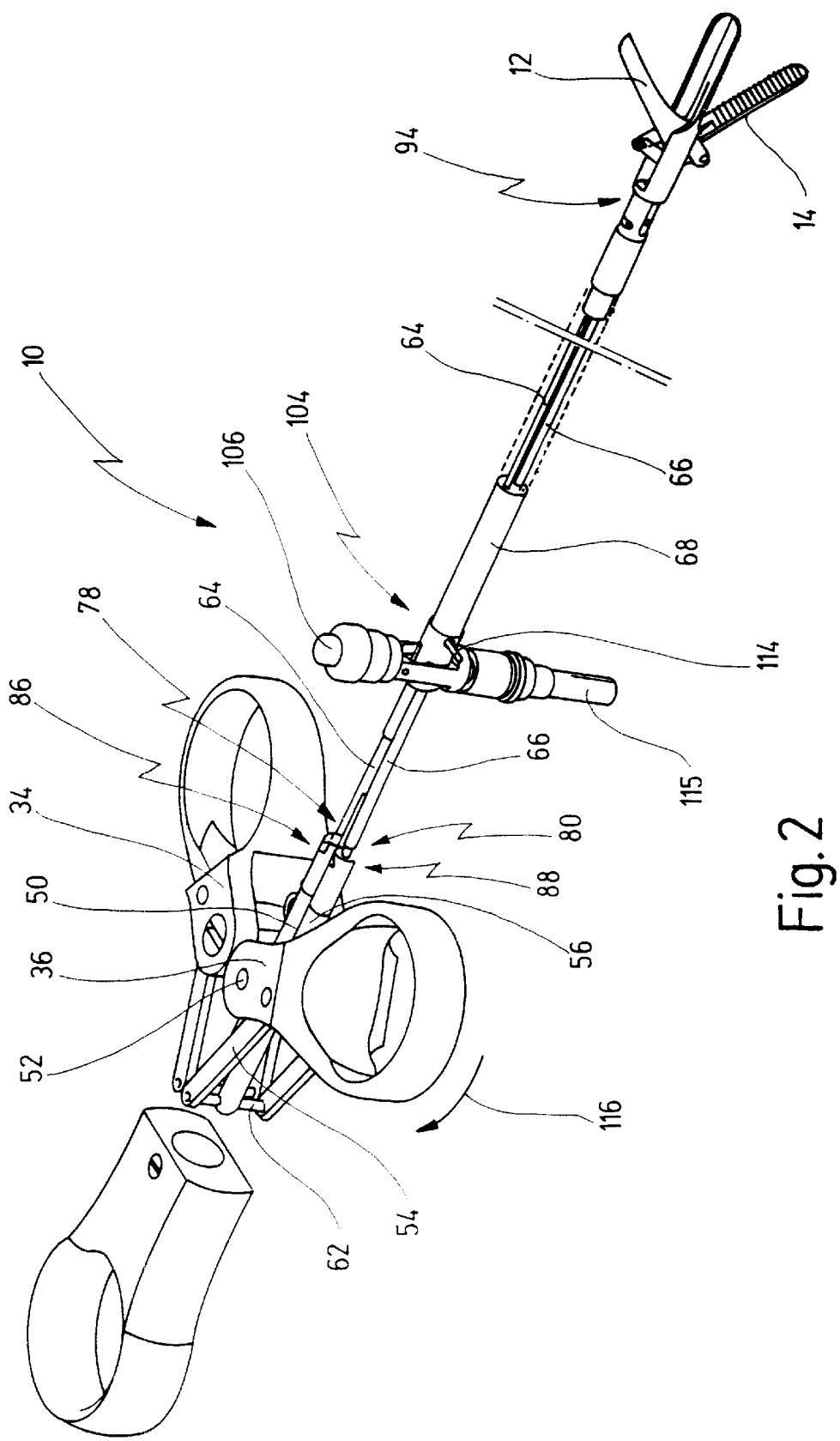
Figure 3:
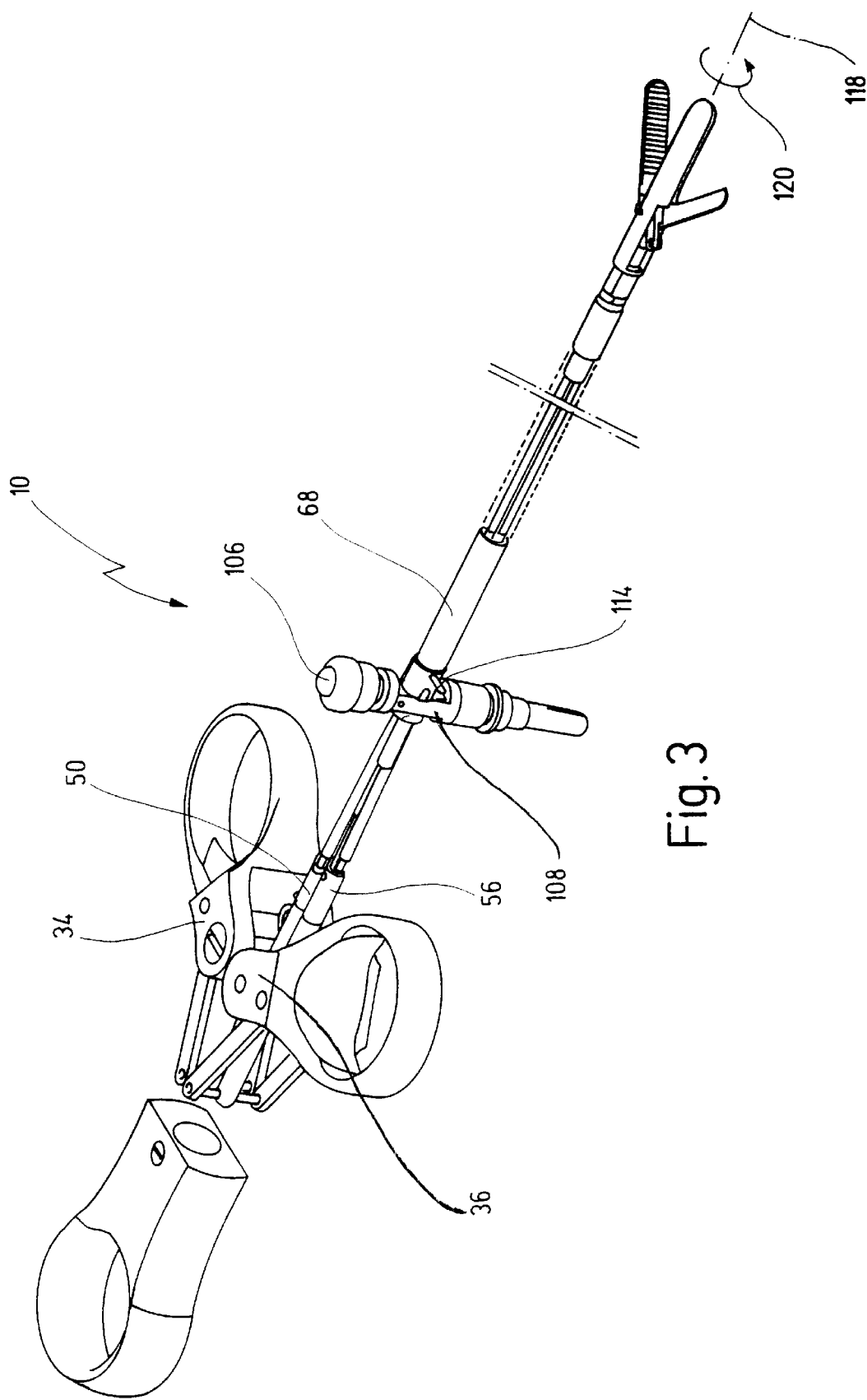
Figure 4:
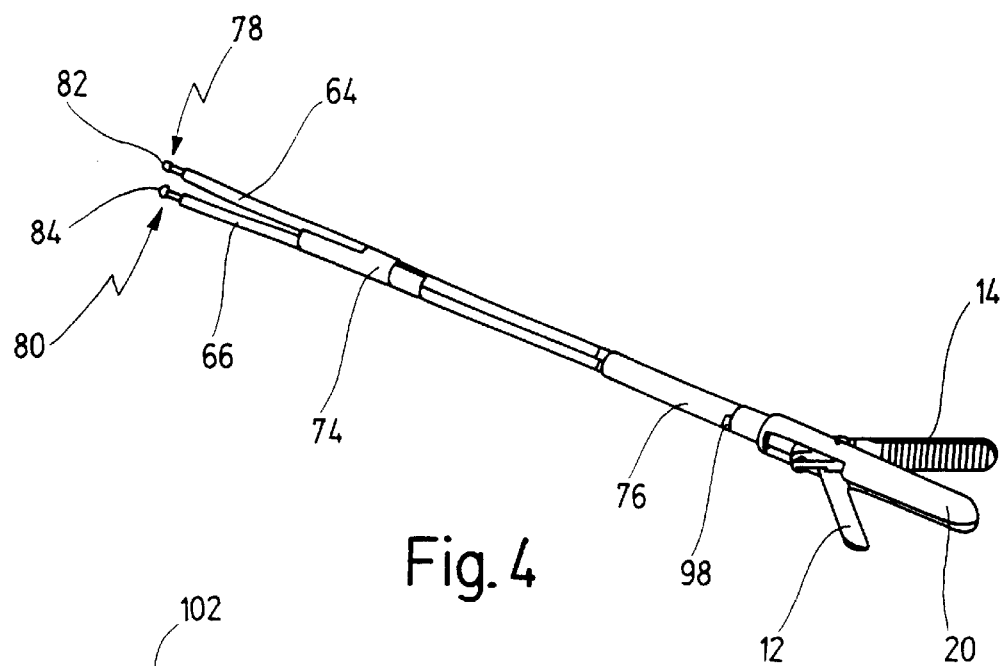
Figure 5:
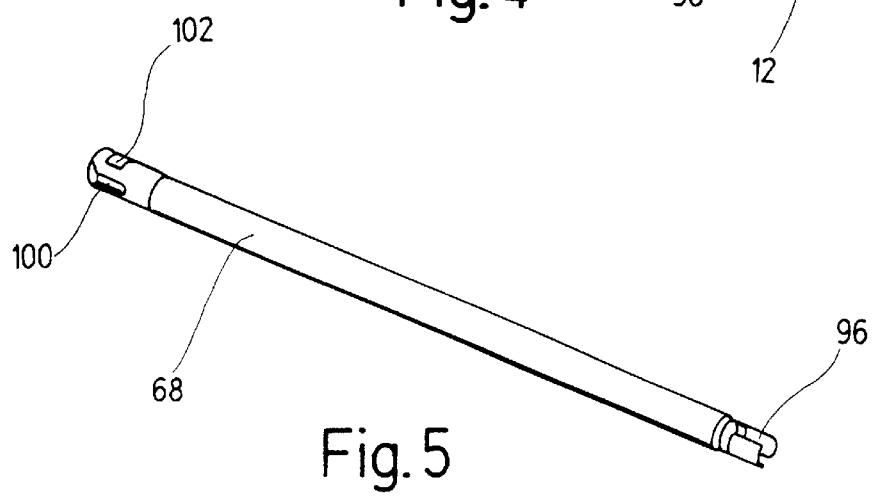
Figure 6:
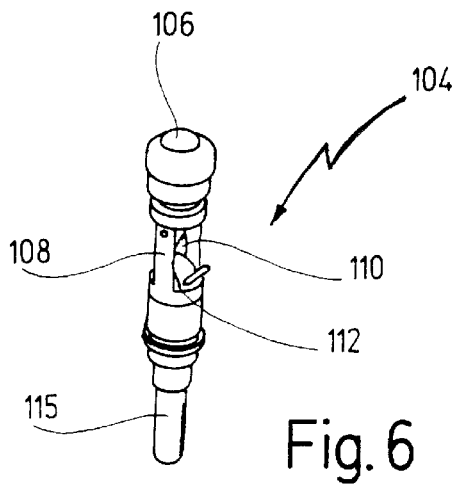

| | |
|---|---|
| FIG. 1 | shows a perspective representation of a forceps according to the present invention; |
| FIG. 2 | shows the forceps in FIG. 1 where the housing is removed; |
| FIG. 3 | shows an illustration of the forceps corresponding to FIG. 2 by which the rods are detached from the actuator elements by rotating the rods; |
| FIG. 4 | shows the assembly composed of the rods and jaw parts of the forceps in FIG. 1 in the condition being removed from the handle; |
| FIG. 5 | shows the shaft of the forceps in FIG. 1 in the condition removed from the handle; |
| FIG. 6 | shows the locking mechanism of the forceps in FIG. 1 for connecting the shaft with the handle; |

Figure 7:
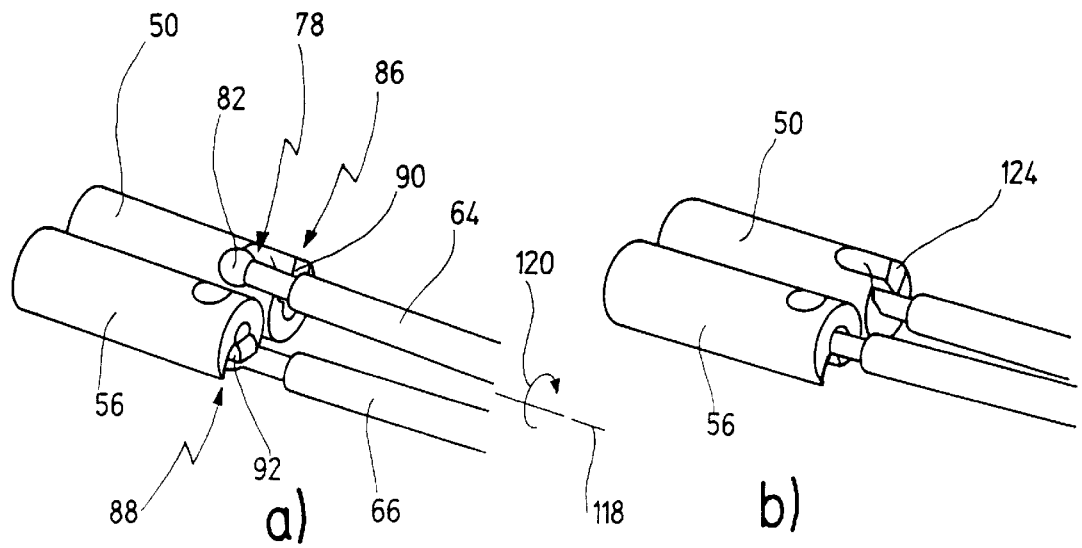
Figure 8:
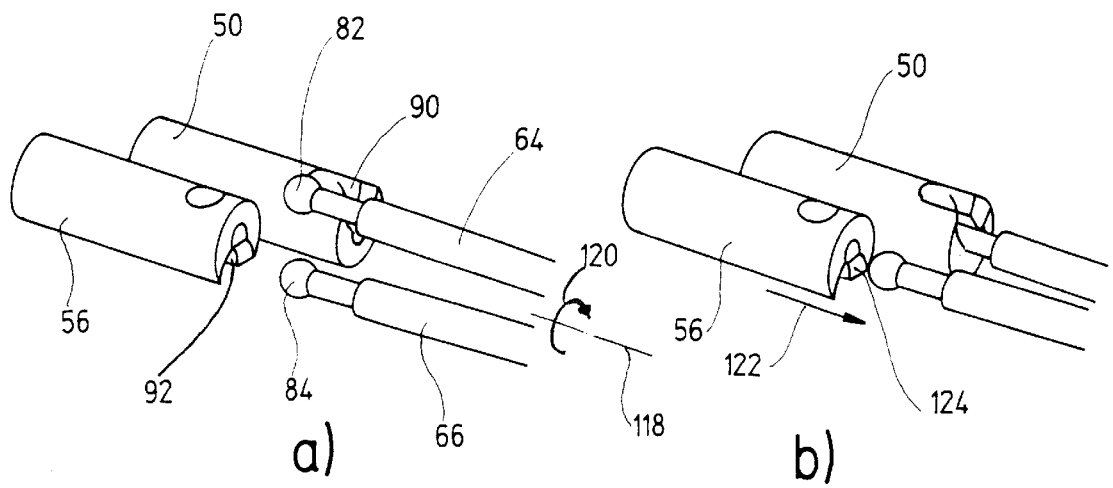

| | |
|---|---|
| Figs. 7a) and 7b) | show the distal portion of the actuator elements and the proximal portion of the rods in enlarged scale in two illustrations, which indicate the connection between the rods and the actuator elements; and |
| Figs. 8a) and 8b) | show the proximal portion of the rods and the distal portion of the actuator elements in enlarged scale in two illustrations, which indicate the connection of the rods with the actuator elements in an alternative manner. |

DETAILED DESCRIPTION OF A PREFERRED EMBODIMENT

A medical forceps is illustrated in FIGS. 1 to 3 with the general reference numeral 10. The forceps 10 comprise a first jaw part 12 and a second jaw part 14 at its distal end. The first jaw part 12 and the second jaw part 14 are moveable independent from one another, i.e. they can be independently opened or closed.

The first jaw part 12 has a cutting function and is formed with a cutting edge 16 for this purpose, which interacts with a cutting edge 18 of an stationary jaw base part 20 when the jaw part 12 is closed in the manner of a scissors. Thus, tissue can be cut and separated from the human or animal body with the jaw part 12.

The second jaw part 14 is formed as a grasping tool and has a serrated surface 22 for this purpose, which interacts with a serrated surface 24 formed on the stationary jaw base part 20 for grasping tissue.

The medical forceps 10 is used in endoscopic surgery for cutting tissue as well as for grasping separated tissue to remove the cut tissue from the body. However, it will be understood that other jaw parts with other functions may be used in the scope of the invention.

The forceps 10 comprise a handle 26 at the proximal end, which includes a housing 28 not shown in FIGS. 2 and 3. A grip 30 fixed to the housing is arranged at the proximal end of the handle 26, which includes a thumb ring 32 through which the surgeon can insert the thumb of one hand for operating the forceps 10.

Further, the handle 26 comprises a first moveable grip 34 as well as a second moveable grip 36. The first moveable grip 34 serves to actuate the first jaw part 12, while the second moveable grip 36 actuates the second jaw part 14. The moveable grips 34, 36 are therefore moveable independently from one another. The first moveable grip 34 comprises a finger ring 38 and the second moveable grip 36 comprises a finger ring 40, through which the surgeon operating the forceps 10 inserts the index finger of the same hand whose thumb he has inserted into the thumb ring 32 to actuate the jaw parts 12 or 14.

The first moveable grip 34 is pivotally mounted to the housing 28 through a hinge joint 42 and the second moveable grip 36 through a hinge joint 44.

A lever link 48 is journaled on the first moveable grip 34 at a point 46, where the lever link 48 is journaled to the first actuator element 50 at its proximal end, which is arranged in the housing 28. The first actuator element 50 is axially displaceable in the housing 28. Correspondingly, a further lever link 54 is journaled to the second moveable grip 36 at the point 52, whose proximal end is also journaled to a second actuator element 56 arranged in the housing parallel to the actuator element 50, which is also axially moveable.

The actuator elements 50, 56 are also axially moveable independent from one another. Two slots 58, 60 are formed in the housing 28 at its distal end, which serve as guide slots for cross pins 62 of the lever links 48, 54, which are passed through the proximal ends of the actuator elements 50, 56.

The first actuator element 50 is joined at its distal end with the proximal end of a first rod 64. The second actuator element 56 is also joined at its distal end with the proximal end of a second rod 66. The rods 64, 66 are round in cross section.

The first rod 64 and the second rod 66 extend adjacently and axially in a shaft 68 out to the distal end of the forceps 10, where the first rod 64 is joined to the first jaw part 12 through a toggle joint arrangement 70 and the second rod 66 to the second jaw part 14 through a toggle joint arrangement 72.

The first rod 64 and the second rod 66, just as the first and second actuator elements 50, 56, are axially displaceable independent from one another within the shaft 68.

The first rod 64 and the second rod 66 are releasably connected to the first actuator element 50 and the second actuator element 56, respectively. Furthermore, the shaft 68 can be removed from the handle 26. The first rod 64 and the second rod 66 together with the jaw parts 12, 14 are shown in FIG. 4 having been removed from the handle 26, while FIG. 5 also shows the shaft 68 alone.

According to FIG. 4, the first rod 64 and the second-rod 66 together with the jaw parts 12, 14 form an assembly. The first rod 64 and the second rod 66 lie parallel to one another and pass through a sleeve 74 surrounding the two rods 64, 66 in which the rods 64, 66 are displaceable and a sleeve 76 at the proximal end of the stationary jaw base part 20. The first rod 64 and the second rod 66 are slightly spread apart from the sleeve 74 to their proximal ends. In addition, the first rod 64 and the second rod 66 are slightly elastically bendable in the mentioned proximal region.

At their proximal ends, the first rod 64 comprises a coupling element 78 and the second rod 66 a coupling element 80. The coupling elements 78, 80 are configured as heads in the form of balls 82, 84. The coupling elements 78, 80 serve to form a force-locking connection of the rods 64, 66 with the actuator elements 50, 56, which comprise corresponding coupling elements 86, 88 configured to be substantially complementary to the coupling elements 78, 80, which comprise bore holes in the form of ball sockets 90, 92 (see especially FIGS. 7 and 8). The coupling mechanism between the rods 64, 66 on the one hand and the actuator elements 50, 56 on the other hand will be described in more detail below.

The assembly formed by the first rod 64, the second rod 66 and the jaw parts 12, 14 is removable from the shaft 68. In the assembled condition, the mentioned assembly is connected to the shaft 68 by a bayonet fastener 94 to be fixed in axial direction (see FIG. 2), however the rods 64, 66 are displaceable relative to the shaft 68. The bayonet fastener 94 is formed by a guide slot 96 at the distal end of the shaft 68, which comprises an axial and a circumferential section and in which a projection 98 (see FIG. 4) formed on the sleeve 76 engages.

The shaft 68 comprises a groove 100 at its proximal end having an axial portion as seen in FIG. 5 and a circumferential portion not shown in FIG. 5. The shaft 68 comprises an approximately rectangular, secant-like notch 102, which is disposed in circumferential direction away from the axial portion of the groove 100. The groove 100 and the notch 102 serve to lock the shaft 68 to the handle 26 by means of a locking mechanism 104 (FIG. 2). The locking mechanism 104 is fixedly connected to the housing 28 of the handle 26.

The locking mechanism 104 is shown alone in FIG. 6. The locking mechanism 104 comprises a button 106 connected with a coupler 108, so that when the button 106 is depressed, the coupler 108 is pushed downwardly as shown in FIG. 3. The depression of the button 106 is countered by the force of a spring, which urges the button 106 and the coupler 108 upwardly into the position shown in FIG. 2.

The coupler 108 has a central opening 110 in which the proximal end of the shaft 68 is passed according to FIG. 2 or FIG. 3. The opening 110 is rounded in the upper region, however in the lower region comprises an inwardly extending projection 112 provided to engage with the notch 102 of the shaft 68. This engagement locks the shaft 68 and the handle 26 to be secured against rotation and against axial displacement, whereby the assembly comprising the first rod 64, the second rod 66 and the jaw parts 12, 14 is secured against rotation and against axial displacement on the handle 26.

The locking mechanism 104 further includes a pin 114 fixed on the inside of the housing 28, which engages with the groove 100 of the shaft 68. In addition, a terminal 115 for connection to a high frequency electric cable is arranged opposite to the button 106.

The jaw parts 12 and/or 14 can thus be supplied with monopolar or bipolar high frequency current. It is also possible to operate the forceps 10 without electricity, or to use the forceps in bipolar operation when corresponding insulation means in the coupling mechanism of the invention is provided between the rods 64, 66 and the actuator elements 50, 56.

Starting with FIG. 2 showing the ready condition of the forceps 10 (where the housing 28 is not shown for better illustration), the function of the forceps 10 as well as the disassembly of the forceps 10 and the assembly of the forceps 10 will be described in more detail in the following.

The moveable grip 34 and the grip 36 are shown in FIG. 2 in their maximum distal pivot position. Corresponding to this position of the grip 34, 36, the first actuator element 50 and the second actuator element 56 and therefore also the first rod 64 and the second rod 66 are also in their maximum distal positions, so that the first jaw part 12 and the second jaw part 14 are in the open position. If for example the first grip 34 is rotated about the hinge joint 44 in the proximal direction shown by the arrow 116, the lever link 54 is urged in proximal direction by this pivot movement, whereby the second actuator element 56 and the second rod 66 are drawn to the proximal direction and the second jaw part 14 is closed. In corresponding manner, the first jaw part 12 can be closed by pivoting the first moveable grip 34 in proximal direction.

To disassemble the forceps 10, the button 106 is first depressed to unlock the locking mechanism 104. By depressing the button 106, the coupler 108 is pushed downwardly, whereby the projection 112 disengages from the notch 102 in the shaft 68. The shaft 68 can now be rotated in the opening 110, in the direction determined by the circumferential portion of the groove 110 in which the pin 114 engages.

By rotating the shaft 68 about its central axis, the first rod 64 and the second rod 66 are rotated about a longitudinal axis 118 as indicated with the arrow 120, whereby the balls 82, 84 at the proximal ends of the rods 64, 66 disengage with the ball sockets 90, 92 at the distal end of the actuator elements 50, 56. For this purpose, the sides of the ball sockets 90, 92 are open, namely the side opening of the ball socket 90 is arranged to be diametrically opposite of the side opening of the ball socket 92. The rotation of the shaft 68 about the longitudinal axis 118 is restricted to an angle of about 90°, since the circumferential portion of the groove 100 of the shaft 68 is provided to have an angular extension of about 90°.

After rotating the shaft 68 and the resultant rotation of the rods 64, 66, which are still angularly fixed to the shaft 68, the shaft 68 and the rods 64, 66 can be removed from the handle 26, or said more precisely can be removed from the housing 28. In the next step, the shaft 68 can be withdrawn from the rods 64, 66 by rotating the shaft 68 with respect to the rods 64, 66 to release the bayonet fastener 94. The rotation of the shaft 68 and the resultant rotation of the rods 64, 66 causing separation of the coupling elements 78, 80 from the coupling elements 86, 88 is possible when the button 106 is depressed, independent of the given axial position of the actuator elements 50, 56, also when the actuator elements 50, 56 are in the maximum distal position as shown in FIG. 3.

The bayonet fastener 94 can only be released when the shaft 68 together with the rods 64, 66 are removed from the handle because the rotational direction for opening the bayonet fastener is opposite to the rotational direction for releasing the balls 82, 84 from the ball sockets 90, 92.

To assemble the shaft 68 and the rods 64, 66 with the handle 26, the disassembly procedure is followed in reverse order.

Initially, the rods 64, 66 are inserted into the shaft 68 until the proximal ends of the rods 64, 66 extend from the proximal end of the shaft 68 and the shaft 68 is secured to the sleeve 76 by means of the bayonet fastener 94. The assembly consisting of the shaft 68 and the rods 64, 66 are then inserted into the distal opening of the housing 26. The pin 114 fixed to the housing engages with the axial portion of the groove 100 of the shaft 68 and ensures that the shaft 68 and therefore the rods 64, 66 are inserted into the housing 26 in a predetermined angular orientation. The button 106 is automatically depressed by passing the proximal end of the shaft 68 through the opening 110 of the locking mechanism 104. The insertion depth of the shaft 68 in the opening 110 is limited by the distal end of the axial portion of the groove 100 in the shaft 68.

After the shaft 68 with the rods 64, 66 is inserted to the maximum position in the housing 28, the balls 82, 84 of the rods 64, 66 are at the angular position shown in FIG. 7a) with respect to the ball sockets 90, 92 of the actuator elements 50, 56. The position shown in FIG. 7a), where the balls 82, 84 are axially at the same level as the ball sockets 90, 92 is reached for example when the actuator elements 50, 56 are both in their maximum distal positions and the rods 64, 66 are urged to their maximum distal positions. In this condition, the balls 82, 84 come into engagement with the ball sockets 90, 92 by rotation of the rods 64, 66 about the longitudinal axis 118 in the direction of the arrow 120 and then become force-locked with one another as shown in FIG. 7b). The spreading of the distal ends of the rods 64, 66 accounts for the lateral spacing of the balls 82, 84 corresponding to the lateral spacing of the ball sockets 90, 92.

The connection of the rods 64, 66 with the actuator elements 50, 56 is however also possible after maximal insertion of the shaft 68 into the housing 28 when the ball 82 and/or the ball 84 is not located at the same axial position as the ball socket 90 and/or the ball socket 92. This is shown in FIG. 8a) with respect to the ball 84 and the ball socket 92.

This situation can for example occur when the actuator element 56 is not in its maximum distal position, while the rod 66 is disposed in its maximum distal position. In this case, when rotating the rods 64, 66 about the longitudinal axis 118 as indicated by the arrow 120, only the ball 82 engages with the socket 90, while the ball 84 is displaced distally from the ball socket 92 as shown in FIG. 8b).

The actuator element 56 in this case is then connected to the rod 66 by pushing the actuator element 56 via the moveable grip 36 in the direction of the distal end as indicated by the arrow 122. The ball socket 92 as well as the ball socket 90 comprises an engagement slope 124 at its end face, whereby the ball 84 engages the engagement slope 124 when shifting the actuator element 56 in the direction of the arrow 122. The proximal end of the rod 66 is slightly deflected due to the elastic bending from its original position transverse to its longitudinal axis and the ball 84 then elastically snaps into the ball socket 92. Thus the rod 66 is then also force-locked with the actuator element 56.

The connection of the rods 64, 66 with the actuator elements 50, 56 is also possible when the two balls 82, 84 after rotation of the rods 64, 66 are located distally before the ball sockets 90, 92, where then the two actuator elements 50, 56 are pushed in the direction of the arrow 122 for producing a force-locking connection with the rods 64, 66.

It can also occur that when inserting the shaft 68 into the housing 26 the balls 82, 84 are located proximally behind the sockets 90, 92. In this case, it is not possible to fully rotate the rods 64, 66 by 90° about the longitudinal axis 118.

The grips 34, 36 are then both pivoted in proximal direction, whereby the actuator elements 50, 56 are withdrawn to the maximal proximal position, so that the balls 82, 84 of the rods 64, 66 are located axially at the same disposition or distally before the ball sockets 90, 92. The rods 64, 66 can now be rotated fully about the longitudinal axis 118 in the direction of the arrow 120, whereafter the actuator elements 50, 56 are returned in the distal direction and, as described above, the balls 82 and 84 lock into the ball sockets 90, 92 by means of the engagement slopes 124.

Although the present forceps 10 in FIGS. 2 and 3 have been described in conjunction with the rods 64, 66 and the actuator elements 50, 56 without illustrating the housing 28, it will be understood that the housing is mounted on the handle 26 when connecting the rods 64, 66 and also when disconnecting the rods 64, 66 with the actuator elements 50, 56. Both the release of the rods 64, 66 from the actuator elements 50, 56 and their connection requires no visual inspection or other external actions.

What is claimed is:

1. Medical forceps, comprising:
a shaft having a distal end and a proximal end;
a first and a second jaw part disposed at said distal end of said shaft and being movable independently from each other;
a handle disposed at said proximal end of said shaft having a first and a second actuator element;
a first and a second rod extending through said shaft and being arranged adjacent to one another and being axially displaceable independently from one another, said first rod being joined to said first jaw part and to said first actuator element and said second rod being joined to said second jaw part and to said second actuator element,
wherein said first rod and said second rod each comprise a coupling element at a proximal end of said first and second rod, said first actuator element and said second actuator element each comprise a coupling element at a distal end of said first and second actuator element, said coupling elements of said actuator element being substantially complementary to said coupling elements of said rods such that said coupling elements of said rods are engageable in force-locking, but releasable manner with said coupling elements of said actuator elements by axially pushing said rods and said actuator elements together.

2. Forceps of claim 1, wherein said coupling elements of said rods and said coupling elements of said actuator elements are configured such that they are disengageable by a rotation of said rods about a longitudinal axis of said shaft.

3. Forceps of claim 1, wherein said coupling elements of said rods become lockingly engaged with said coupling elements of said actuator elements by actuating said actuator elements and/or by actuating said jaw parts.

4. Forceps of claim 1, wherein said coupling elements of said rods and/or said coupling elements of said actuator elements comprise engagement slopes.

5. Forceps of claim 4, wherein said rods are slightly elastically bendable at said proximal ends thereof.

6. Forceps of claim 1, wherein said rods are restricted against undesired rotation when said coupling elements of said rods are engaged with said coupling elements of said actuator elements.

7. Forceps of claim 1, wherein said shaft is joined to said handle in detachable manner.

8. Forceps of claim 7, wherein said shaft is joined to said handle by means of a locking mechanism arranged on said handle.

9. Forceps of claim 8, wherein said locking mechanism secures said shaft against rotation.

10. Forceps of claim 1, wherein said shaft is removable from said rods and wherein said rods are secured against rotation with said shaft in an assembled condition.

11. Forceps of claim 1, wherein said coupling elements of said rods are formed as heads and said coupling elements of said actuator elements are formed as substantially complementary bore holes, which are open on a distal front side of said actuator elements and are open to a side, or vice versa.

12. Forceps of claim 11, wherein said bore holes are formed as ball sockets, and said side opening of said first ball socket is directed in said opposite direction with respect to said side opening of said second ball socket.

13. Forceps of claim 1, wherein said coupling elements of said rods are engageable in force-locking, but releasable manner with said coupling elements of said actuator elements by commonly rotating said rods about a longitudinal axis of said shaft.

14. Medical forceps, comprising:
a shaft having a distal end and a proximal end;
a first and a second jaw part disposed at said distal end of said shaft and being movable independently from each other;
a handle disposed at said proximal end of said shaft having a first and a second actuator element;
a first and a second rod extending through said shaft and being arranged adjacent to one another and being axially displaceable independently from one another, said first rod being joined to said first jaw part and to said first actuator element and said second rod being joined to said second jaw part and to said second actuator element,
wherein said first rod and said second rod each comprise a coupling element at a proximal end of said first and second rod, said first actuator element and said second actuator element each comprise a coupling element at a distal end of said first and second actuator element, said coupling elements of said actuator element being substantially complementary to said coupling elements of said rods such that said coupling elements of said rods are engageable in force-locking, but releasable manner with said coupling elements of said actuator elements by commonly rotating said rods about a longitudinal axis of said shaft.

15. Forceps of claim 14, wherein said coupling elements of said rods and said coupling elements of said actuator elements are configured such that they are disengageable by a rotation of said rods about said longitudinal axis.

16. Forceps of claim 14, wherein said coupling elements of said rods become lockingly engaged with said coupling elements of said actuator elements by actuating said actuator elements and/or by actuating said jaw parts.

17. Forceps of claim 14, wherein said coupling elements of said rods and/or said coupling elements of said actuator elements comprise engagement slopes.

18. Forceps of claim 17, wherein said rods are slightly elastically bendable at said proximal ends thereof.

19. Forceps of claim 14, wherein said rods are restricted against undesired rotation when said coupling elements of said rods are engaged with said coupling elements of said actuator elements.

20. Forceps of claim 14, wherein said shaft is joined to said handle in detachable manner.

21. Forceps of claim 20, wherein said shaft is joined to said handle by means of a locking mechanism arranged on said handle.

22. Forceps of claim 21, wherein said locking mechanism secures said shaft against rotation.

23. Forceps of claim 14, wherein said shaft is removable from said rods and wherein said rods are secured against rotation with said shaft in an assembled condition.

24. Forceps of claim 14, wherein said coupling elements of said rods are formed as heads and said coupling elements of said actuator elements are formed as substantially complementary bore holes, which are open on a distal front side of said actuator elements and are open to a side, or vice versa.

25. Forceps of claim 24, wherein said bore holes are formed as ball sockets, and said side opening of said first ball socket is directed in said opposite direction with respect to said side opening of said second ball socket.

26. Forceps of claim 14, wherein said coupling elements of said rods are engageable in force-locking, but releasable manner with said coupling element of said actuator elements by axially pushing said rods and said actuator elements together.

* * * * *